United States Patent [19]
Nguyen et al.

[11] Patent Number: 5,503,036
[45] Date of Patent: Apr. 2, 1996

[54] OBSTRUCTION DETECTION CIRCUIT FOR SAMPLE PROBE

[75] Inventors: Dinh Nguyen, Wellington; Frank Robb, Amherst, both of Ohio

[73] Assignee: Ciba Corning Diagnostics Corp., Medfield, Mass.

[21] Appl. No.: 239,625

[22] Filed: May 9, 1994

[51] Int. Cl.$^6$ .............................. G01N 1/14; G01N 35/10
[52] U.S. Cl. .................... 73/864.34; 73/864.11; 340/608; 340/625
[58] Field of Search ..................... 340/608, 626; 73/863.01, 863.02, 863.03, 864.11, 864.21, 864.81, 864.85, 864.86, 864.87, 864.34

[56] References Cited

U.S. PATENT DOCUMENTS

| | | | |
|---|---|---|---|
| 3,972,614 | 8/1976 | Johansen et al. | 356/36 |
| 3,976,989 | 8/1976 | Smith | 340/626 X |
| 4,030,888 | 6/1977 | Yamamoto et al. | 356/39 X |
| 4,072,934 | 2/1978 | Hiller et al. | 340/608 |
| 4,090,129 | 5/1978 | Gear | 222/132 X |
| 4,093,849 | 6/1978 | Baxter, Jr. et al. | 235/92 PC |
| 4,103,229 | 7/1978 | Gear . | |
| 4,157,498 | 6/1979 | Johnson . | |
| 4,160,373 | 7/1979 | Fastaia et al. | 340/608 X |
| 4,165,484 | 8/1979 | Haynes | 235/92 PC X |
| 4,218,610 | 8/1980 | Baxter, Jr. et al. | 235/92 PC |
| 4,662,540 | 5/1987 | Schroter | 340/606 X |
| 4,671,123 | 6/1987 | Magnussen et al. | 73/864.16 |
| 4,696,183 | 9/1987 | Mitsumaki et al. | 73/863.01 X |
| 4,710,163 | 12/1987 | Butterfield | 604/65 |
| 4,729,876 | 3/1988 | Hennessy et al. | 422/103 |
| 4,743,228 | 5/1988 | Butterfield | 604/50 |
| 4,893,515 | 1/1990 | Uchida | 73/864.34 |
| 4,959,050 | 9/1990 | Bobo, Jr. | 604/49 |
| 4,967,753 | 11/1990 | Haase et al. | 128/662.06 |
| 5,006,309 | 4/1991 | Khalil et al. | 422/56 |
| 5,032,362 | 7/1991 | Marsoner et al. | 422/81 |
| 5,204,525 | 4/1993 | Hillman et al. | 250/252.1 |

FOREIGN PATENT DOCUMENTS

| | | |
|---|---|---|
| 0052355 | 5/1982 | European Pat. Off. . |
| 0169071 | 1/1986 | European Pat. Off. . |
| 0199466 | 10/1986 | European Pat. Off. . |
| 0215534 | 3/1987 | European Pat. Off. . |

(List continued on next page.)

OTHER PUBLICATIONS

Patent Abstracts of Japan; v.004, n.032; Mar. 19, 1980; & JP-A-55 004117.

Patent Abstracts of Japan; v.007, n.216; Sep. 24, 1983; & JP-A-58 108473.

IBM Technical Disclosure Bulletin; v.34, n.9; Feb. 2, 1992; p. 374-380; XP 00030/916.

"Infusion Line Model for the Detection of Infiltration, extravasation, and other Fluid Flow Faults", by T. S. Harris, et al., IEEE Transactions on Biomedical Engineering, vol. 40, No. 2, Feb. 1993 pp. 154–162.

"Abbott Prism: A Multichannel Heterogeneous Chemiluminescence Immunoassay Analyzer", by O. S. Khalil, et al., Clinical Chemistry, vol. 37, No. 9, 1991 pp. 1540–1547.

*Primary Examiner*—Thomas P. Noland
*Attorney, Agent, or Firm*—Nicholas I. Slepchuk, Jr.; Arthur S. Morgenstern; Judith A. Roesler

[57] ABSTRACT

An obstruction detection circuit for detecting an obstruction of a sample probe of an automated sample aspiration/dispensation device and a method for detecting such an obstruction. In one embodiment the obstruction detection circuit includes a pressure sensor measuring the pressure in a fluid conduit connecting a pump and the sample probe orifice. The pressure within the connecting fluid conduit is measured by the pressure sensor shortly after the start of the aspiration or dispensation of a fluid volume by the automated sample aspiration/dispensation device. The pressure within the connecting fluid conduit is again measured after the completion of the aspiration or dispensation, and if the pressure has not returned to a predetermined range within a predetermined amount of time, an error condition is reported.

14 Claims, 6 Drawing Sheets

FOREIGN PATENT DOCUMENTS

| | | |
|---|---|---|
| 0341438 | 11/1989 | European Pat. Off. . |
| 0571100 | 11/1993 | European Pat. Off. . |
| 0569213 | 11/1993 | European Pat. Off. . |
| 2443274 | 3/1976 | Germany . |
| 1515574 | 6/1978 | United Kingdom . |
| WO89/10193 | 11/1989 | WIPO . |
| WO92/08545 | 5/1992 | WIPO . |

OBSTRUCTION DETECTION CIRCUIT FOR SAMPLE PROBE

FIELD OF THE INVENTION

The invention relates to the field of automated fluid sample aspiration/dispensation devices and more particularly, to devices for detecting an obstruction in the sample probe of an automated fluid sample aspiration/dispensation device.

TECHNICAL REVIEW

Automated analyzers are used in clinical laboratories to measure the various chemical constituents of body fluids, such as whole blood, blood serum, blood plasma, cerebral spinal fluid, and urine, obtained from patients. Automated analyzers reduce the number of trained technicians required to perform the analyses in a clinical laboratory, improve the accuracy of the testing and reduce the cost per test.

Typically, an automated analyzer includes an automated fluid sample aspiration/dispensation device which automatically aspirates a sample of fluid from a patient's specimen container and dispenses the sample into a reaction cuvette. The analyzer may also dispense reagents, which are specific for the test being performed, into a cuvette or reaction container thereby mixing the sample with the reagents. By examining the reaction products resulting from the reaction of the test sample and reagents, the automated analyzer determines the concentration of the specific chemical constituent or analyte, for which the testing is being performed, in the patient's specimen. Upon completion of the test, the automated analyzer typically reports/prints the results of the test, including sample identifier, the numerical result of the test, and the normal range of values for the chemical constituent or analyte as measured by the test.

A problem that occurs with such automated analyzers is that occasionally upon aspirating a sample, a blood clot or other debris can obstruct, partially or fully, the sample probe of the automated fluid sample aspiration/dispensation device, preventing the necessary sample volume of the specimen from being aspirated or from being completely dispensed into the reaction cuvette. If an improper sample volume of specimen is mixed with the reagents, an incorrect test result will typically be determined.

Generally, when a clinician obtains an unusual test result, or when the laboratory technologist directly or indirectly notes an abnormal result, the test is repeated and the new result compared to the previous result. If the two results do not agree to within a predetermined limit, the test must be repeated a second time in order to determine which of the previous two results is valid.

Thus, it is desirable that the automated fluid sample aspiration/dispensation device provide some means for determining the presence of an obstruction in the sample probe so that the technologist performing the test can be informed that a test result is invalid due to an obstruction in the sample probe.

The invention relates to an obstruction detection circuit for detecting an obstruction of a sample probe of an automated fluid sample aspiration/dispensation device and a method for detecting such an obstruction. In one embodiment, the obstruction detection circuit includes a pressure sensor measuring the pressure in a fluid conduit connecting a pump and to a sample probe orifice. The pressure within the connecting fluid conduit is measured shortly after the start of the aspiration or dispensation of a sample volume by the automated fluid sample aspiration/dispensation device. The pressure within the connecting fluid conduit is again measured after the completion of the aspiration or the dispensation by the pump, and if the pressure has not returned to a predetermined range within a predetermined amount of time, an error condition is reported.

The invention also describes a method for determining whether a sample probe of an automated fluid sample aspiration/dispensation device is obstructed, said method comprising the steps of beginning one of a dispensation or an aspiration of a volume of fluid through said sample probe; completing said one of a dispensation or an aspiration of said volume of fluid through said sample probe; measuring a final pressure within said sample probe at a predetermined amount of time following said completion of said one of dispensation or an aspiration; and signaling an error condition if said final pressure within said sample probe is outside a predetermined range.

The invention also describes a sensor for a fluid aspirate/dispense probe comprising an obstruction detection circuit operatively connected to said sensor; and a controller operatively connected to said obstruction detection circuit, wherein said obstruction detection circuit responds to pressure changes at said sensor and wherein pressure changes beyond a defined range or baseline causes said circuit to signal an error to said controller.

The invention also describes a sensor for a fluid aspirate/dispense probe comprising an obstruction detection circuit operatively connected to said sensor; and a controller operatively connected to said obstruction detection circuit, wherein said obstruction detection circuit responds to pressure changes at said sensor and wherein pressure changes occuring beyond a defined time limit causes said circuit to signal an error to said controller.

DESCRIPTION OF THE DRAWINGS

This invention is pointed out with particularity in the appended claims. The above and further advantages of this invention may be better understood by referring to the following description taken in conjunction with the accompanying drawing, in which:

DETAILED DESCRIPTION OF THE INVENTION

Figure 1:
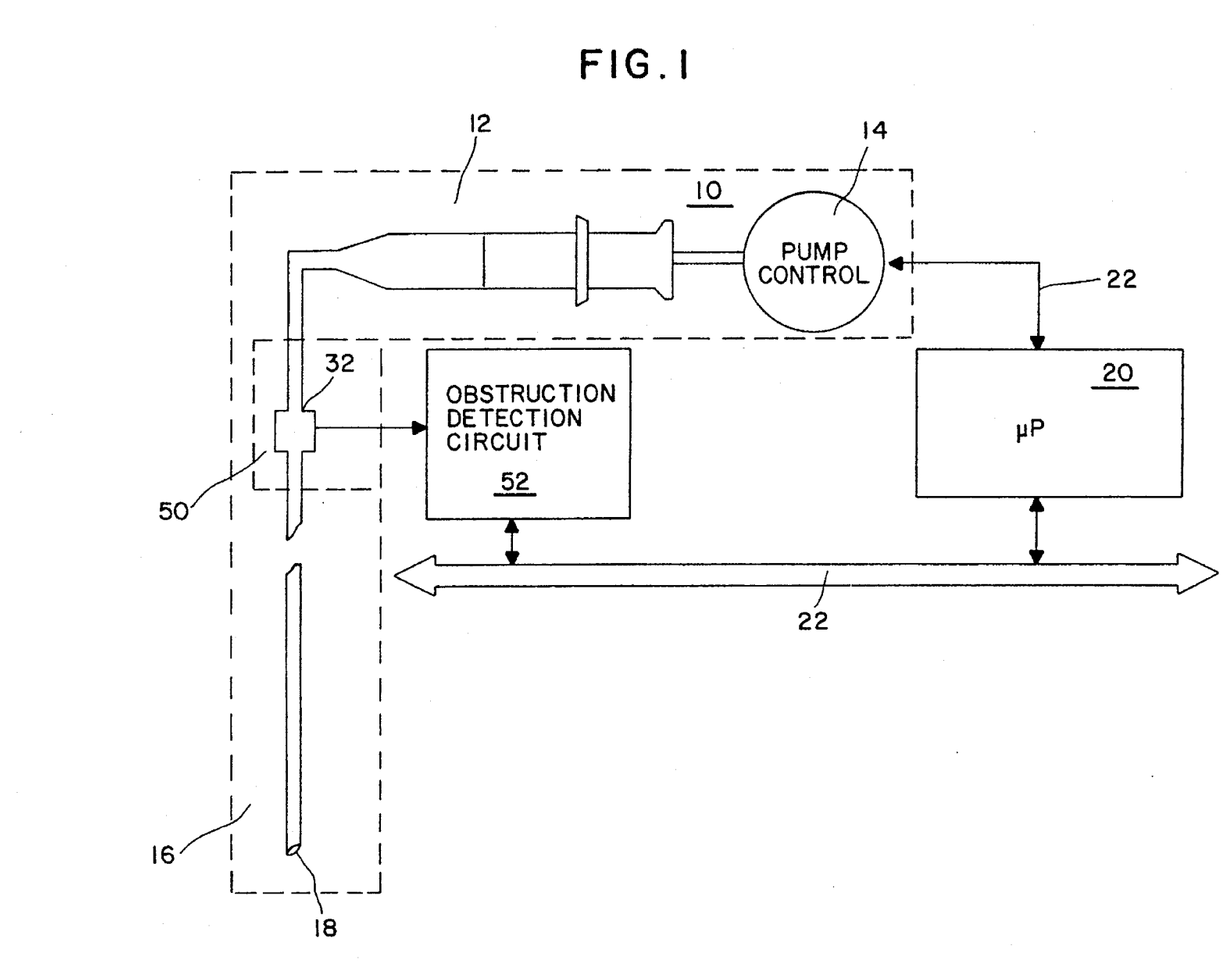
FIG. 1 is a block diagram of the obstruction detection circuit of the invention used in conjunction with an automated fluid sample aspiration/dispensation device.

Referring to FIG. 1, and in brief overview, the obstruction detection circuit 52 of the invention is depicted in conjunction with an automated fluid sample aspiration/dispensation device. An automated fluid sample aspiration/dispensation device 10 including a pump 12, shown here in the form of a syringe pump, a pump controller 14 and a fluid conduit 16 having a sample probe orifice 18, is controlled by and provides operational data to a microprocessor 20 by means of a databus 22. In one embodiment, microprocessor 20 is an Intel i8051 8 bit microprocessor with a 16 MHz clock.

A pressure sensor 50 is located inline with the fluid conduit 16 between sample probe orifice 18 and the pump 12. The pressure sensor 50 is located as near to the pump 12 and as far from sample probe orifice 18 as possible to improve the signal to noise ratio of the pressure measurement. Pressure sensor 50 is electrically connected to the obstruction detection circuit 52 which is electrically connected to microprocessor 20 by means of the databus 22. Thus, as pump 12 aspirates or dispenses a sample volume, pressure changes in the fluid conduit 16 between pump 12 and sample probe orifice 18 are measured by pressure sensor 50 and monitored by obstruction detection circuit 52. If an obstruction of the sample probe orifice 18 or the fluid conduit 16 occurs, obstruction detection circuit 52 transmits the presence of the obstruction to microprocessor 20.

Figure 2:
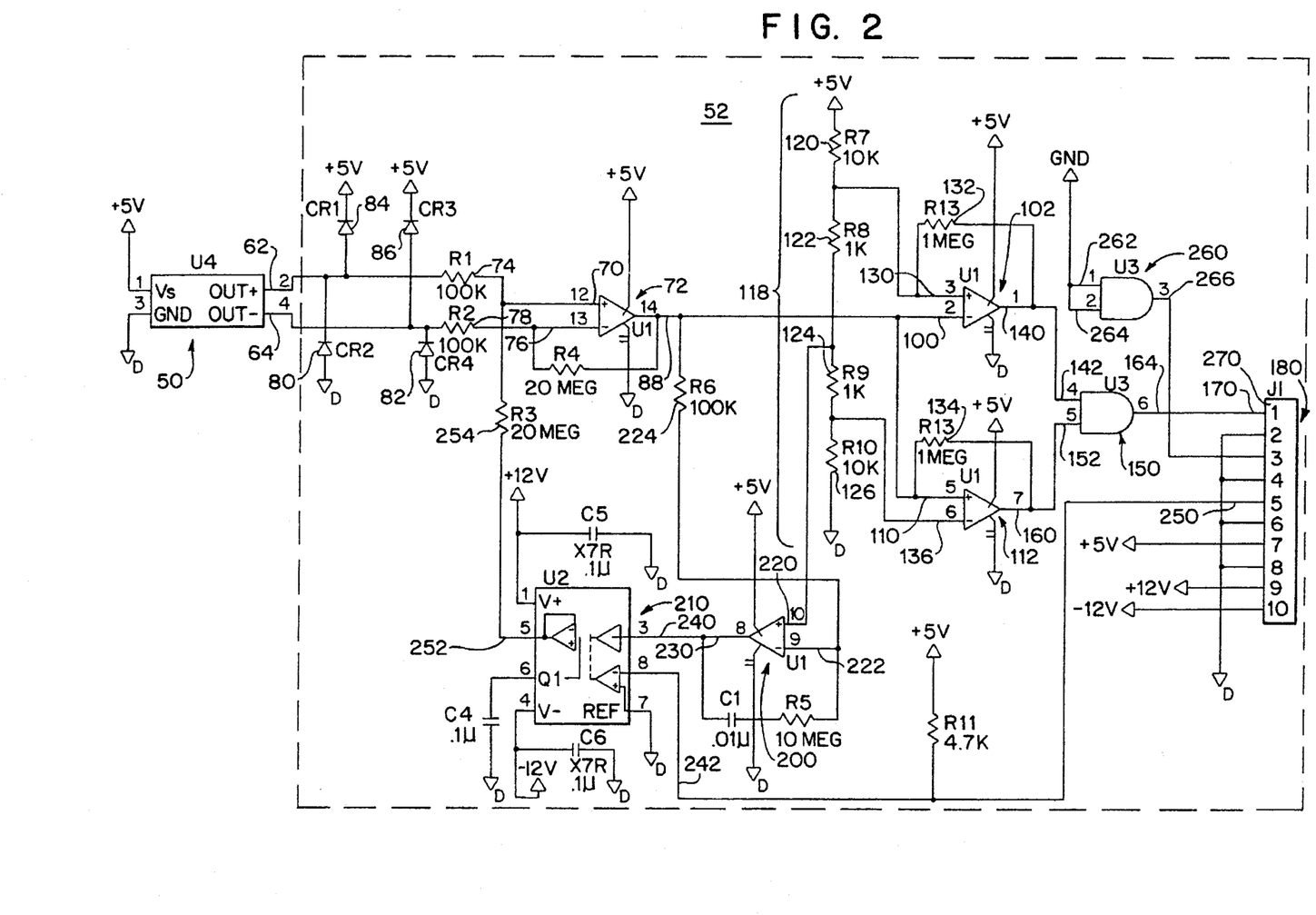
FIG. 2 is a schematic diagram of an embodiment of the obstruction detection circuit of the invention.

In more detail, and referring also to FIG. 2, an embodiment of the obstruction detection circuit 52 of the invention is in electrical communication with pressure sensor 50. Pressure sensor 50 produces a differential output voltage on its output terminals 62, 64 proportional to the pressure difference between the pressure in the fluid conduit 16 and ambient atmospheric pressure.

In particular, pressure sensor 50 has a positive output terminal 62 and a negative output terminal 64. The voltage between the positive output terminal 62 and ground and the negative output terminal 64 and ground is proportional to the pressure measured by the pressure sensor 50. In one embodiment, pressure sensor 50 is a 26PC series pressure sensor manufactured by the Microswitch Division of Honeywell Inc., Freeport, Ill., which produces a change in output voltage of about 6.67 mV/PSI of pressure difference.

Positive output terminal 62 of pressure sensor 50 is connected to the positive input terminal 70 of differential amplifier 72 through resistor 74. Negative output terminal 64 of pressure sensor 50 is connected to the negative input terminal 76 of differential amplifier 72 through a resistor 78. Four diodes 80, 82, 84, 86 connected in pairs between positive output terminal 62 and negative output terminal 64 and a 5.0 V supply (diodes 84, 86) and between positive output terminal 62 and negative output terminal 64 and ground (diodes 80, 82) provide electrostatic discharge (esd) protection for the circuit. It should be noted that one output terminal, for example 64, of pressure sensor 50 may be grounded (or a single output pressure sensor may be used) and differential amplifier 72 replaced with a single input amplifier without affecting the operation of the circuit.

Output terminal 88 of differential amplifier 72 is connected to the negative input terminal 100 of upper limit pressure signal comparator 102 and to the positive input terminal 110 of lower limit pressure signal comparator 112. A voltage divider 118, in one embodiment of resistors 120 (10 kΩ), 122 (1 kΩ), 124 (1 kΩ) and 126 (10 kΩ) connected between ground and a 5.0 V supply, provides the reference voltages both for upper limit pressure signal comparator 102 and for the lower limit pressure signal comparator 112. Positive input terminal 130 of upper limit pressure signal comparator 102 is connected to the junction of resistors 120 and 122 of voltage divider 118, thus providing a reference voltage of 2.75 V at the positive input terminal 130 for the embodiment of voltage divider 118 shown. Similarly, negative input terminal 136 of comparator 112 is connected to the junction of resistors 124 and 126 of voltage divider 118, thus providing a reference voltage of 2.25 V at the negative input terminal 136 for the embodiment of voltage divider 118 shown.

Output terminal 140 of upper limit pressure signal comparator 102 is connected to positive input terminal 130 through a resistor 132 to provide a predetermined amount of hysteresis. Similarly output terminal 160 of lower limit pressure signal comparator 112 is connected to positive input terminal 110 through a resistor 134, again to provide a predetermined amount of hysteresis. Output terminal 140 of upper limit pressure signal comparator 102 is also connected to one input terminal 142 of AND gate 150. The other input terminal 152 of AND gate 150 is connected to output terminal 160 of lower limit pressure signal comparator 112. Output terminal 164 of AND gate 150 is connected to one terminal 170 of multiterminal connector 180 which connects to databus 22 of microprocessor 20. The microprocessor 20 monitors the voltage level of terminal 170 at predetermined times to determine if an obstruction of the sample probe orifice 18 or the fluid conduit 16 is present.

A servo-loop including amplifier 200 and sample-and-hold circuit 210 provides a known signal level to the positive input 70 of differential amplifier 72 when sample-and-hold circuit 210 is sampling. Positive input terminal 220 of error amplifier 200 is connected to the junction of resistors 122 and 124 of voltage divider 118 which provides a reference voltage of 2.5 V to the positive input terminal 220 of amplifier 72 for the values of the resistors in the embodiment of the voltage divider 118 shown. The negative input terminal 222 of amplifier 200 is connected to the output terminal 88 of amplifier 72 through resistor 224. The output terminal 230 of amplifier 200 is connected to the signal input terminal 240 of sample-and-hold circuit 210.

The control terminal 242 of sample-and-hold circuit 210 is connected to a second terminal 250 in connector 180. Microprocessor 20 controls the sample-and-hold circuit 210 by controlling the signal level to terminal 250 of connector 180. The output terminal 252 of sample-and-hold circuit 210 is connected to the positive terminal 70 of differential amplifier 72 through resistor 254.

In the embodiment shown, each data line to microprocessor 20 includes a pull-up resistor and hence each data line is maintained in a signal high state unless pulled to a signal low state by a device on the databus 22. The obstruction detection circuit 52 includes a second AND gate 260 which has both its input terminals 262, 264 connected to ground to provide a low output signal on output terminal 266 at all times. This output terminal 266 is connected to a terminal 270 of connector 180 and pulls the corresponding data line low to indicate to microprocessor 20 that the obstruction detection circuit 52 is present in the aspiration/dispension device. It should be noted that it is also possible to connect both input terminals 262, 264 to 5.0 V supply and thereby produce a high signal on terminal 270 of AND gate 282 to provide an indication that the obstruction detection circuit 52 is present in the case where data lines of the microprocessor system are not normally high.

In general, the operating principle of obstruction circuit 52 is that upon aspiration, the pressure in the connecting fluid conduit 16 will decrease as the pump 12 creates a partial vacuum so as to draw the fluid sample into the fluid conduit 16 through the sample probe orifice 18. Once the aspiration has completed, the pressure in the fluid conduit 16 will return to normal as atmospheric pressure forces the fluid sample into the fluid conduit 16, and the system pressure equilibrates. However, if sample probe orifice 18 or the fluid conduit 16 is obstructed, for example by a blood clot or other debris, the fluid sample will be prevented, to some degree, from entering the fluid conduit 16 and hence the pressure within the connecting fluid conduit 16 will remain below atmospheric pressure or a defined pressure range after aspiration has completed.

Similarly, upon dispensation, the pressure in the connecting fluid conduit 16 will increase as pump 12 increases the pressure on the fluid sample to expel the sample from the connecting fluid conduit 16 out through the sample probe orifice 18. Once the dispensation has completed, the pressure in the fluid conduit 16 will again return to atmospheric pressure as the sample is dispensed and the system pressure equilibrates. However, if the sample probe orifice 18 or the fluid conduit 16 is obstructed, all or some of the sample fluid will be prevented from leaving the fluid conduit 16 and, therefore, the pressure within connecting fluid conduit 16 will remain above atmospheric pressure or a defined pressure range after the dispensation has completed.

Thus by measuring the pressure within the connecting fluid conduit 16 after aspiration or dispensation has completed, obstruction detection circuit 52 can determine if the pressure has returned to within the normal range. If the pressure in the fluid conduit 16 has not returned to atmospheric pressure or a defined pressure range within a predetermined amount of time following the completion of aspiration or dispensation, the fluid conduit 16 is reported to be obstructed.

In more detail, pressure sensor 50 produces a positive or negative differential voltage (depending upon whether the pressure is increasing or decreasing) on its output terminals 62, 64 proportional to the pressure sensed. In the embodiment shown, as pump 12 aspirates a sample volume, the pressure in fluid conduit 16 decreases, the voltage on output terminal 62 (measured relative to ground) decreases, and the voltage on output terminal 64 (measured relative to ground) increases, from a set value of 2.5 V, the voltage (relative to ground) on each output terminal 62,64 when ambient atmospheric pressure is measured. Conversely, as pump 12 dispenses a sample volume, the pressure in connecting fluid conduit 16 increases, the voltage on output terminal 62 (measured relative to ground) increases and the voltage on output terminal 64 (measured relative to ground) decreases from the set value of 2.5 V. The voltage on output terminals 62, 64 of pressure sensor 50 is amplified by differential amplifier 72 which produces an output signal on output terminal 88 which is proportional to the pressure difference sensed. This output signal from differential amplifier 72 is one input signal to the negative input terminal 100 of high limit pressure signal comparator 102 and the positive input terminal 110 of low limit pressure signal comparator 112.

When the input signal to the negative input terminal 100 of high limit pressure signal comparator 102 exceeds the reference voltage of 2.75 V supplied by the voltage divider 118 to the positive terminal 130, the output signal on output terminal 140 of high limit comparator 102 goes low thereby applying a low input signal to input terminal 142 of AND gate 150 causing the output signal on the output terminal 164 of AND gate 150 to go low.

Similarly, when the output signal of differential amplifier 72 applied to positive input terminal 110 of low limit pressure signal comparator 112, falls below the reference voltage of 2.25 V applied to the negative input terminal 136 of low limit pressure signal comparator 112 as provided by voltage divider 118, the output signal on output terminal 160 of the low limit pressure signal comparator 112 goes low thereby applying a low input signal to input terminal 152 of AND gate 150 and causing the output signal on output terminal 164 of AND date 150 to go low.

Hence the output signal of AND gate 150 will go low if the pressure sensed by sensor 150 is outside the predetermined range either above a predetermined value or below a predetermined value. By examining the state of the output signal on output terminal 164 of AND gate 150, one can determine whether the signal from differential amplifier 72 (and hence whether the pressure detected by pressure sensor 50) is outside the limits as determined by the reference voltages on the high and low limit pressure comparators 102 and 112, respectively.

The amplified pressure signal from output terminal 88 of differential amplifier 72 is the input signal to the negative input terminal 222 of error amplifier 200. Positive terminal 220 of amplifier 200 is connected to a 2.5 V reference voltage also supplied by voltage divider 118. The difference between the input signal on negative input terminal 222 and the 2.5 V reference voltage on positive input terminal 220 constitutes an error signal which is produced on output terminal 230 of amplifier 200.

The error signal is applied to input terminal 240 of sample-and-hold circuit 210. When control line 242 of sample-and-hold circuit 210 is high, the sample-and-hold circuit 210 is sampling and the error signal on the input terminal 240 of the sample-and-hold circuit 210 appears on output terminal 252 of sample-and-hold circuit 210.

Thus, when sample-and-hold circuit 210 is sampling, the signal on output 252 of sample-and-hold circuit 210 is added to the output voltage from positive output terminal 62 of pressure sensor 50 at positive input terminal 70 of differential amplifier 72. Thus error amplifier 200 acts as an error amplifier in a servo-loop which forces the output of the differential amplifier 72 to 2.5 V when sample-and-hold circuit 210 is sampling. This provides a 2.5 V baseline to comparators 102 and 112.

Once the signal on control terminal 242 of sample-and-hold circuit 210 goes low, sample-and-hold circuit 210 stops sampling, and the last error signal prior to the cessation of sampling on input terminal 240 of sample-and-hold circuit 210 appears on output terminal 252 of sample-and-hold circuit 210 to establish a signal voltage baseline corresponding to ambient pressure.

Once the voltage baseline is established, voltage deviations from this baseline, due to pressure changes measured by pressure sensor 50, are compared to reference voltages by comparators 102 and 112 as discussed previously. Thus, obstruction detection circuit 52 first establishes a baseline voltage corresponding to equilibrium pressure conditions and then measures pressure changes from this baseline.

Figure 3:
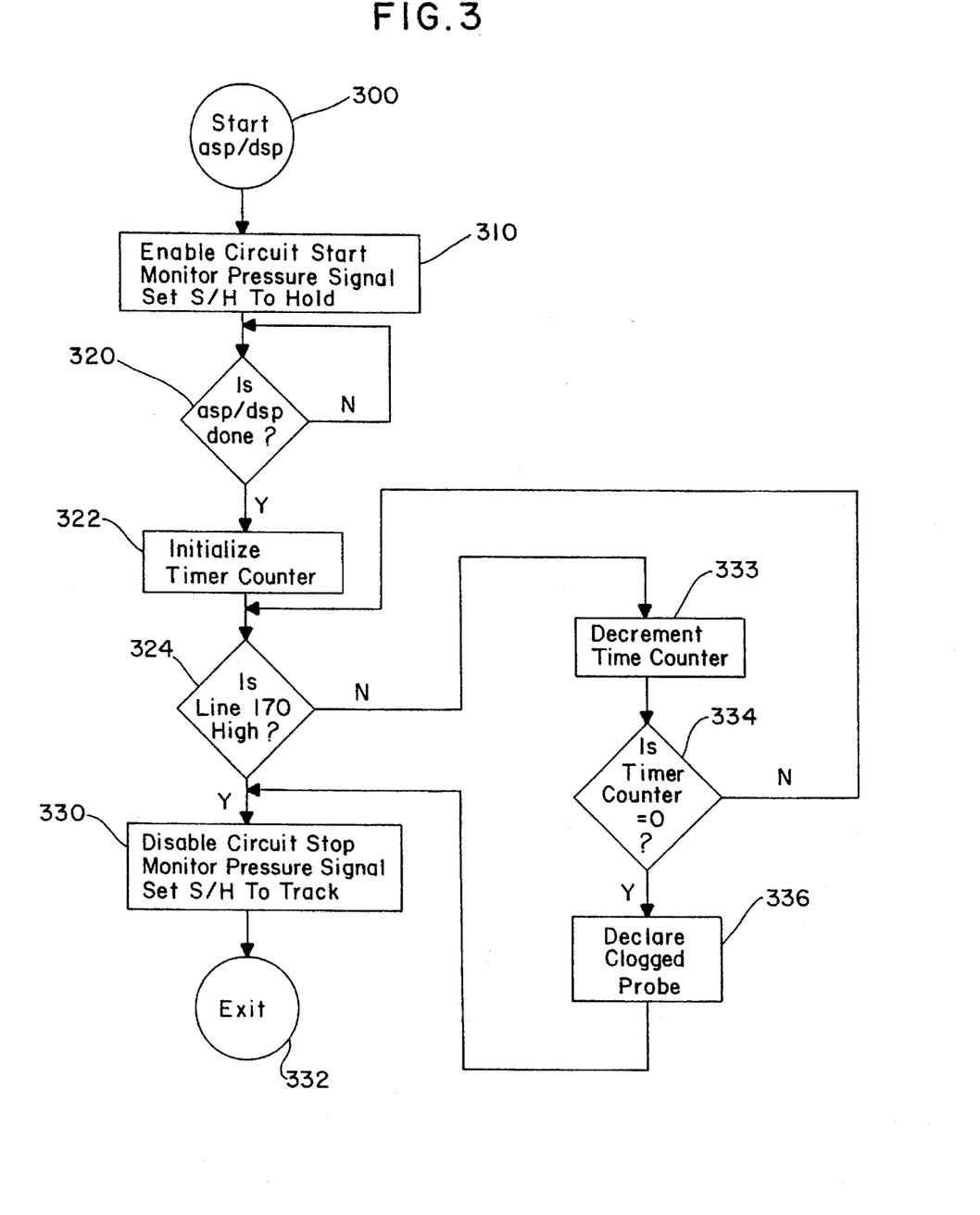
FIG. 3 is a flow diagram of an embodiment of an algorithm used in conjunction with the embodiment of the circuit shown in FIG. 2, to detect the presence of an obstruction in the sample probe.

FIG. 3 depicts a preferred embodiment of an algorithm which is used by the microprocessor 20 for monitoring the state of the output signal of AND gate 150 by way of terminal 170. Microprocessor 20 begins the monitoring routine by causing pump 12 to begin aspirating or dispensing a sample (step 300). As aspiration or dispensation of the sample is begun, pressure within the fluid path conduit 16 begins to change.

At the same time, once aspiration or dispensation has begun, microprocessor 20 places (step 310) a low logic voltage on terminal 250 of connector 180 thereby causing sample-and-hold circuit 210 to hold the current value of the voltage applied to its input terminal 240 on its output terminal 252. This removes the effect of the servo-loop, thereby letting the differential amplifier 72 amplify the pressure signal from the pressure sensor 50 and enabling obstruction detection circuit 52 to monitor the changes in pressure in the fluid conduit 16.

Microprocessor 20 then loops (step 320) until the aspiration or dispensation by pump 12 is completed. Once pump 12 has completed the aspiration or dispensation, microprocessor 20 loads a register (step 322) that will act as a countdown timer. The value loaded in the register corresponds to an elapsed time of 110 msec when the register counts down to 0 from its initial value.

Microprocessor 20 then determines (step 324) if the signal on terminal 170 of connector 180 is high. If the signal on terminal 170 is high, indicating that the output signal from AND gate 150 is high, and therefore the pressure in the fluid conduit 16 is neither above nor below the permissible limits, the microprocessor 20 sets line 250 high (step 330) thereby instructing sample-and-hold circuit 210 to begin sampling. This in effect disables the obstruction detection circuit 52 by preventing it from monitoring the pressure in the fluid conduit 16. The program then exits (step 332) until the start of the next aspiration or dispensing cycle.

If the signal on terminal 170 of connector 180 is set low, indicating that the output of AND gate 150 is low (and hence that the pressure within the fluid conduit 16 is above or below the permissible limits), microcomputer 20 then decrements the elapsed time counter (step 333) and checks (step 334) whether the elapsed time counter has counted down to zero. If the elapsed time timer has not counted down to zero, indicating that the 110 msec of elapsed time has not completed and hence that the system has not yet stabilized, microprocessor 20 returns in the loop to again check the state of the signal on terminal 170 of connector 180.

If the elapsed time is in excess of 110 msec, thereby indicating that the pressure within the system should be stable, and if the state of the signal on terminal 170 is low, indicating that the pressure in the fluid conduit 16 remains above a permissible limit after a dispensation or remains below a permissible limit after an aspiration, microprocessor 20 determines that this is an error condition caused by an obstruction in fluid path 16, notifies the operator or signals the error condition (step 336), sets (step 330) the sample-and-hold circuit 210 to sample and exits (step 332).

Thus, microprocessor 20 monitors the pressure at the start and at the end of fluid sample aspiration or dispensation. If the pressure in the fluid conduit 16 does not return to within a permissible range following the fluid sample aspiration or dispensation within a predetermined amount of time, the obstruction detection circuit 52 indicates such and microprocessor 20 is notified of the error condition.

Figure 3A:
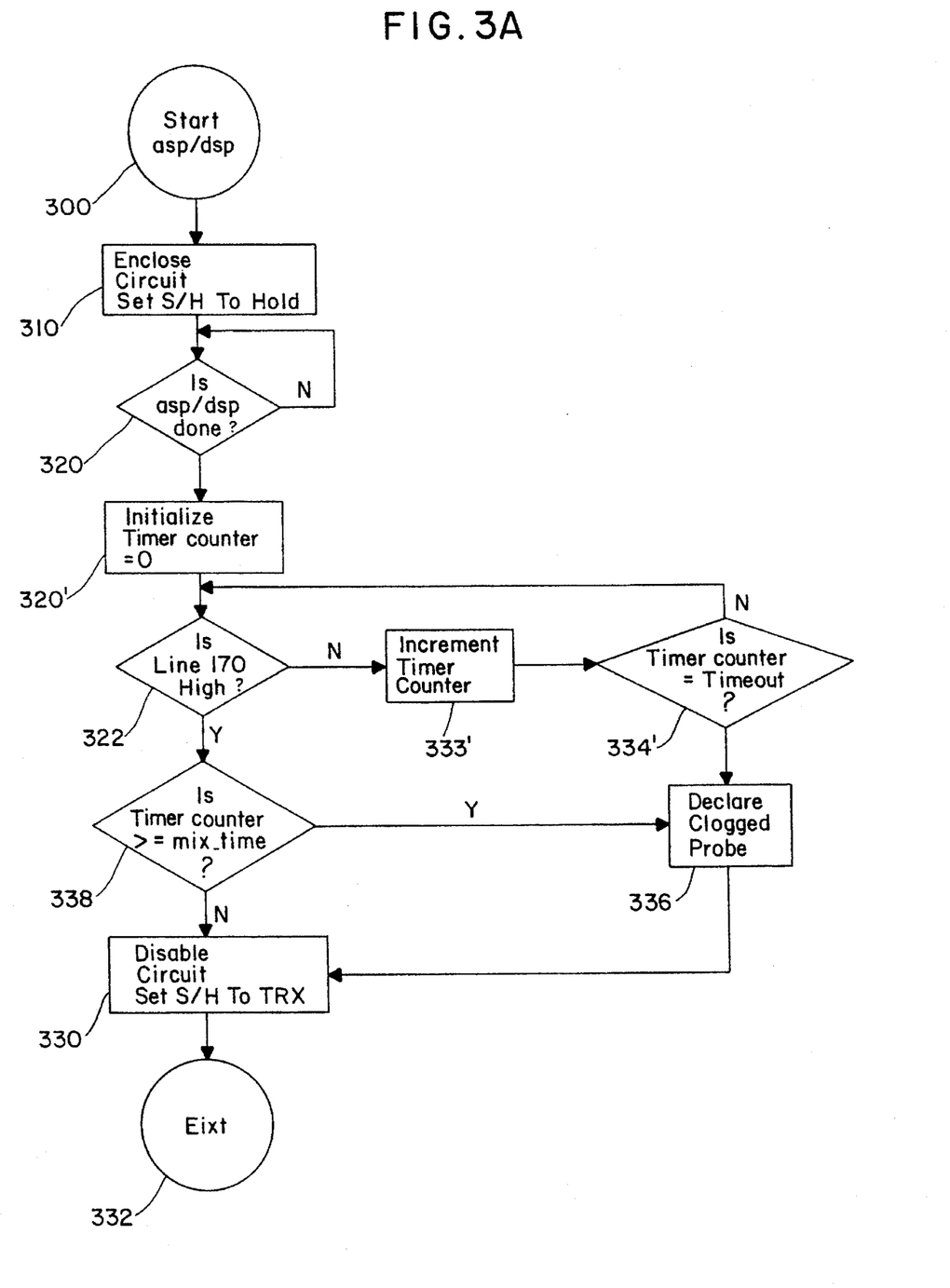
FIG. 3a is a flow diagram of another embodiment of an algorithm used in conjunction with the embodiment of the circuit shown in FIG. 2, to detect the presence of an obstruction in the sample probe.

FIG. 3a depicts another embodiment of an algorithm which is used by microprocessor 20 to determine if the pressure is outside the normal limits at predetermined times. Specifically, the microprocessor 20 in this embodiment measures the amount of time required for the pressure in the fluid conduit 16 to return to the normal range. If the time to return to the normal range is greater than a predetermined max-time, in this case 110 msec, then the fluid conduit 16 is determined to be at least partially clogged. If the fluid conduit 16 is so clogged that the pressure never returns to the normal range, the microprocessor 20 will measure a time greater than or equal to a timeout value, and then declares or signals the fluid conduit 16 clogged.

In more detail, in this embodiment, after the aspiration or dispensation is completed (step 320), the timer counter is initialized to 0 (step 320') and line 170 is checked to determine if the pressure in the fluid conduit 16 is within the normal range (step 322). If the pressure in the fluid conduit 16 is outside the normal range, the timer counter is incremented (step 333') and the timer counter is checked to see if it is equal to or exceeds the timeout value (step 334'). If the microprocessor 20 has timedout, the fluid conduit 16 is declared clogged (step 336), the circuit is disabled (step 330) and the algorithm exits (step 332), as in the previous embodiment. Otherwise the loop continues.

Once the pressure has been determined to have returned to the normal range (step 322), the timer is checked to determine if it has returned within the allowable max-time (step 338). If the pressure has returned to the normal range within the allowable time, the circuit is disabled (step 330) as in the other embodiment and the algorithm exits (step 332). If the pressure returns to within the normal range in a time greater than the allowable max-time, the fluid conduit is declared as clogged (step 336) prior to the circuit being disabled (step 330).

Figure 4:
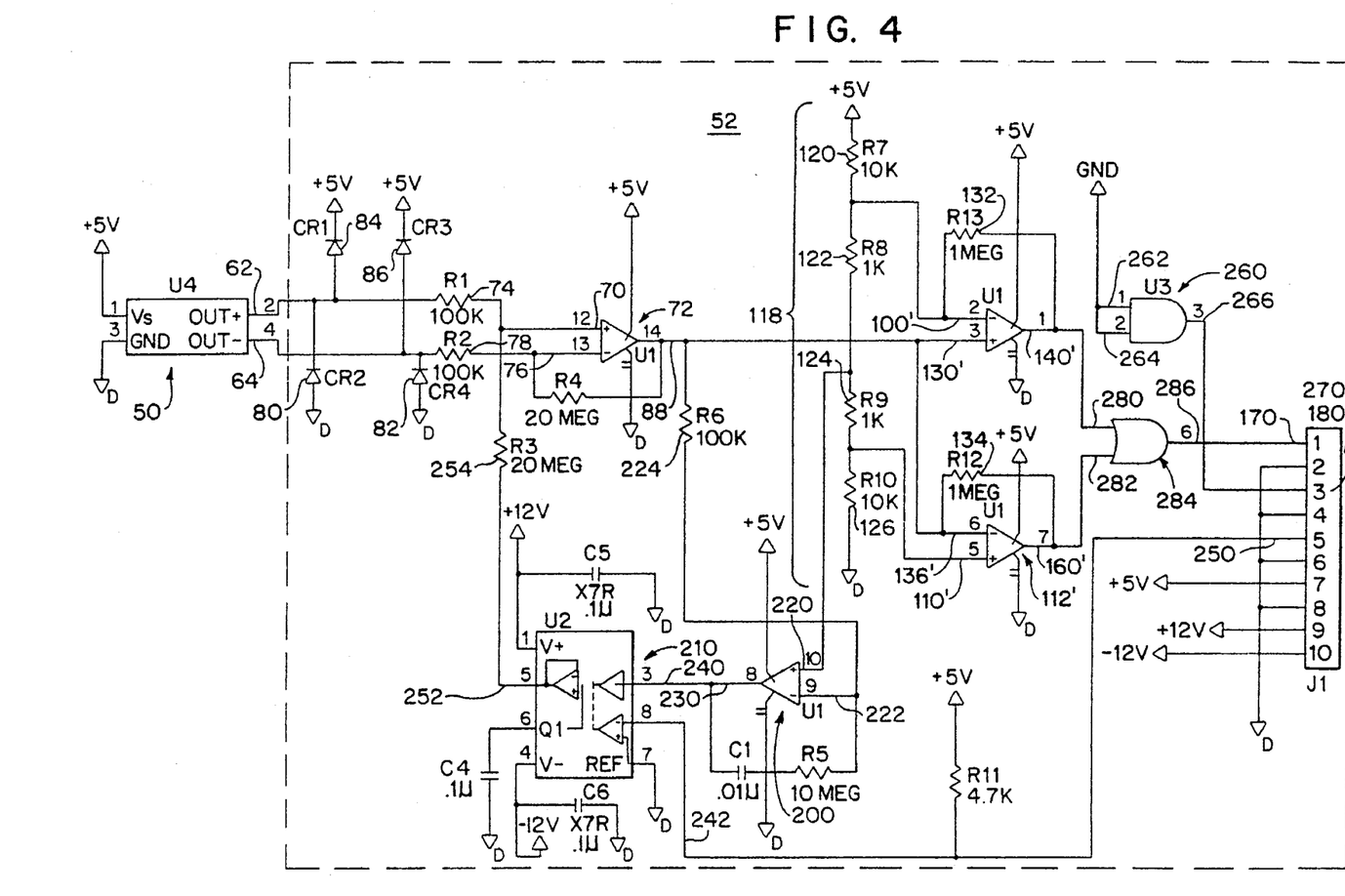
FIG. 4 is a schematic diagram of another embodiment of the obstruction detection circuit of the invention.

FIG. 4 depicts another embodiment of the obstruction detection circuit 52'. This embodiment is similar to the embodiment shown in FIG. 2, with the exception that the input signals to the individual comparators 102' and 112' have been reversed. That is, the output signal from the differential amplifier 72 is the input signal to positive input terminal 130' of high pressure signal limit comparator 102' and negative input terminal 136' of low pressure signal limit comparator 112', and the reference voltage from voltage divider 118 is the input signal to negative input terminal 100' of high pressure signal limit comparator 102' and positive input terminal 110' of low pressure limit signal comparator 112'. The output terminals 140' and 160' of comparators 102' and 112', respectively, are connected to input terminals 280 and 282, respectively, of OR gate 284. The output terminal of OR gate 286 is connected to terminal 170 of connector 180.

Thus unlike the circuit depicted in FIG. 2, when the input signal to the positive input terminal 130' of high limit pressure signal comparator 102' exceeds the reference voltage of 2.75 V supplied by the voltage divider 118 to the negative terminal 100', the output signal on output terminal 140' of high limit comparator 102' goes high, thereby applying a high input signal to input terminal 280 of OR gate 284 causing the output signal on the output terminal 286 of OR gate 284 to go high. Similarly, when the output signal of differential amplifier 72 applied to positive input terminal 110' of low limit pressure signal comparator 112', falls below the reference voltage of 2.25 V applied to the negative input terminal 136' of low limit pressure signal comparator 112' as provided by voltage divider 118, the output signal on output terminal 160' of the low limit pressure signal comparator 112' goes high thereby applying a high input signal to input terminal 282 of OR gate 284 and causing the output signal on output terminal 286 of OR date 284 to go high.

Hence the output signal of OR gate 284 will go high if the pressure sensed by sensor 150 is outside the predetermined range. By examining the state of the output signal on output terminal 286 of OR gate 284, microprocessor 20 can determine whether the signal from differential amplifier 72 outside of the acceptable range and hence whether the pressure detected by pressure sensor 50 is outside the limits as determined by the reference voltages on the high and low limit pressure comparators 102' and 112', respectively. It should be noted that in this embodiment microprocessor 20 determines that the pressure within the fluid conduit is outside the desired range by observing that the voltage at terminal 170 of connector 180 is high rather than low.

Figure 5:
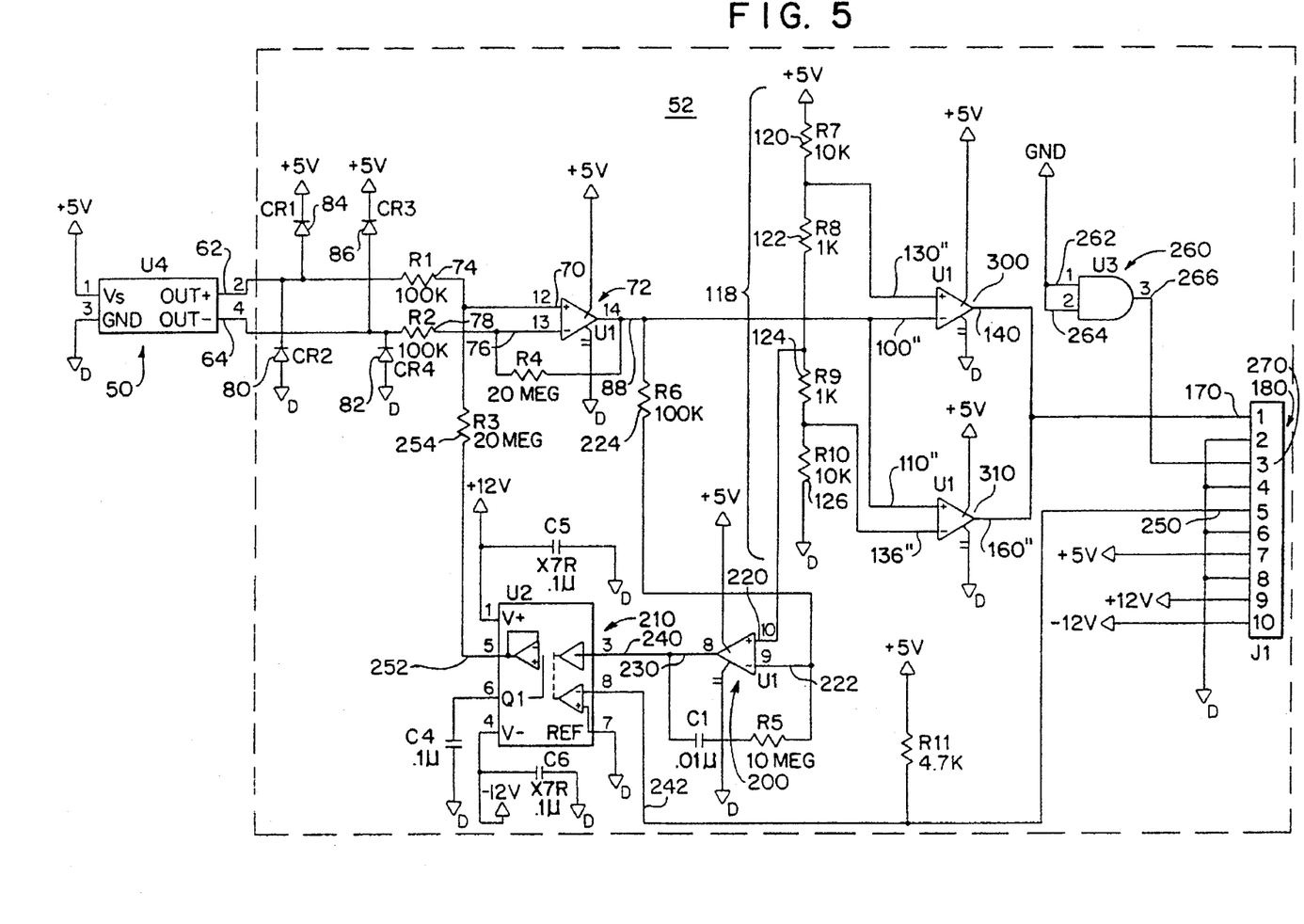
FIG. 5 is a schematic diagram of another embodiment of the obstruction detection circuit of the invention.

FIG. 5 depicts another embodiment where comparators 102 and 112 have been replaced by tri-state comparators 300 and 310. The positive input terminal 130" of tri-state comparator 300 is connected to a reference voltage from voltage divider 118. The negative input terminal 100" is connected to the output terminal 88 of differential amplifier 72. Similarly, the negative input terminal 136" of tri-state comparator 310 is connected to a reference voltage from voltage divider 118 and the positive input terminal 110" is connected to the output terminal 88 of differential amplifier 72. The configuration of the circuit is similar to that described above with respect to FIG. 2. In this embodiment however, output terminal 140" of tri-state comparator 300 and the output terminal 160" of tri-state comparator 310 are connected together and to terminal 170. The use of tri-state comparators 300, 310 permit the output terminals of 140", 160", the comparators 300, 310 respectively to be connected together without the use of intervening logic gates such as AND gate 150.

Finally it should be noted that each of the embodiments shown may be configured with the output terminals of the comparators being directly connected to separate terminals in connector 180. In this way the signals on both of the output terminals of the comparators can be examined individually by microprocessor 20 to determine if the signal from the pressure sensor 50 is out of range. However, this embodiment then requires two data lines to be used to communicate with the microprocessor 20 rather than the single data line (connected to terminal 170) of the previous embodiments. Additionally, the microprocessor 20 would then have to check each line individually to determine an error condition, rather than the single determination of the signal state of terminal 170 is done in the previous embodiments of the invention.

Having shown the preferred embodiment, those skilled in the art will realize many variations are possible which will still be within the scope and spirit of the claimed invention. Therefore, it is the intention to limit the invention only as indicated by the scope of the claims.

We claim:

1. A method for determining whether a sample probe of an automated fluid sample aspiration/dispensation device is obstructed, said method comprising the steps of:

beginning one of a dispensation or an aspiration of a volume of fluid through said sample probe;

completing said one of a dispensation or an aspiration of said volume of fluid through said sample probe;

measuring a final pressure within said sample probe at a predetermined amount of time following said completion of said one of a dispensation or an aspiration; and signaling an error condition if said final pressure within said sample probe is outside a predetermined range.

2. A sample probe obstruction detection device for detecting an obstruction in a sample probe of an automated fluid sample aspiration/dispensation device having said sample probe, a pump and a fluid conduit connecting said sample probe and said pump, said sample obstruction detection device comprising:

a pressure sensor having a first output terminal, said pressure sensor positioned to measure pressure in said fluid conduit, said pressure sensor producing a signal representative of a pressure in said fluid conduit on said first output terminal; and an obstruction detection circuit having a first input terminal in electrical communication with said first output terminal of said pressure sensor;

said obstruction detection circuit providing a first signal on an output terminal of said obstruction detection circuit if said pressure sensor measures a pressure in said fluid conduit which is outside a predetermined pressure range at a predetermined amount of time following completion of one of an aspiration and a dispensation by said pump.

3. The sample probe obstruction detection device of claim 2 wherein said obstruction detection circuit comprises:

a high limit pressure signal comparator having a first input terminal in electrical communication with said first output terminal of said pressure sensor, a second input terminal in electrical communication with a first predetermined reference voltage, and an output terminal; and a low limit pressure signal comparator having an input terminal in electrical communication with said first output terminal of said pressure sensor, a second input terminal in electrical communication with a second predetermined reference voltage and an output terminal, said high limit pressure signal comparator producing a first out of range signal on said output terminal of said high limit pressure signal comparator when pressure in said fluid conduit is higher than a predetermined value, said low limit pressure signal comparator producing a second out of range signal on said output terminal of said low limit pressure signal comparator when pressure in said fluid conduit is lower than a predetermined value.

4. The sample probe obstruction detection circuit, of claim 3 further comprising an amplifier having a first input terminal in electrical communication with said first output terminal of said pressure sensor and an output terminal in electrical communication with said first input terminal of said high limit pressure comparator and in electrical communication with said first input terminal of said low limit pressure signal comparator.

5. The sample probe obstruction detection circuit of claim 4 wherein said pressure sensor includes a second output terminal and said amplifier is a differential amplifier, said differential amplifier further having a second input terminal in electrical communication with said second output terminal of said pressure sensor.

6. The sample probe obstruction detection circuit of claim 3 further comprising a determination circuit having a first input terminal in electrical communication with said output terminal of said high limit pressure signal comparator, a second input terminal in electrical communication with said output terminal of said low limit pressure signal comparator and an output terminal, said determination circuit producing a third out of range signal when either said high limit pressure output comparator produces a first out of range signal or said low limit pressure output comparator produces a second out of range signal.

7. A sample probe obstruction detection device for detecting an obstruction in a sample probe of an automated fluid sample aspiration/dispensation device having said sample probe, a pump, and a fluid conduit connecting said sample probe and said pump, said sample obstruction detection device comprising:

a pressure sensor having a first output terminal, said pressure sensor positioned to measure pressure in said fluid conduit, said pressure sensor producing a signal representative of a pressure in said fluid conduit on said first output terminal;

an obstruction detection circuit providing a signal if said pressure sensor measures a pressure in said fluid conduit which is outside a predetermined pressure range at a predetermined amount of time following completion of one of an aspiration and a dispensation by said pump, said obstruction detection circuit comprising:

a high limit pressure signal comparator having a first input terminal in electrical communication with said first output terminal of said pressure sensor, a second input terminal in electrical communication with a first predetermined reference voltage, and an output terminal; and a low limit pressure signal comparator having an input terminal in electrical communication with said first output terminal of said pressure sensor, a second input terminal in electrical communication with a second predetermined reference voltage and an output terminal, said high limit pressure signal comparator producing a first out of range signal on said output terminal of said high limit pressure signal comparator when pressure in said fluid conduit is higher than a predetermined value, said low limit pressure signal comparator producing a second out of range signal on said output terminal of said low limit pressure signal comparator when pressure in said fluid conduit is lower than a predetermined value; and a determination circuit having a first input terminal in electrical communication with said output terminal of said high limit pressure signal comparator, a second input terminal in electrical communication with said output terminal of said low limit pressure signal comparator and an output terminal, said determination circuit producing a third out of range signal when either said high limit pressure output comparator produces a first out of range signal or said low limit pressure output comparator produces a second out of range signal, wherein said determination circuit is an AND gate having a first input terminal in electrical communication with said output terminal of said high limit pressure signal comparator, a second input terminal in electrical communication with said output terminal of said low limit pressure signal comparator, and an output terminal.

8. A sample probe obstruction detection device for detecting an obstruction in a sample probe of an automated fluid sample aspiration/dispensation device having said sample probe, a pump, and a fluid conduit connecting said sample probe and said pump, said sample obstruction detection device comprising:

a pressure sensor having a first output terminal, said pressure sensor positioned to measure pressure in said fluid conduit, said pressure sensor producing a signal representative of a pressure in said fluid conduit on said first output terminal;

an obstruction detection circuit providing a signal if said pressure sensor measures a pressure in said fluid conduit which is outside a predetermined pressure range at a predetermined amount of time following completion of one of an aspiration and a dispensation by said pump, said obstruction detection circuit comprising:

a high limit pressure signal comparator having a first input terminal in electrical communication with said first output terminal of said pressure sensor, a second input terminal in electrical communication with a first predetermined reference voltage, and an output terminal; and a low limit pressure signal comparator having an input terminal in electrical communication with said first output terminal of said pressure sensor, a second input terminal in electrical communication with a second predetermined reference voltage and an output terminal, said high limit pressure signal comparator producing a first out of range signal on said output terminal of said high limit pressure signal comparator when pressure in said fluid conduit is higher than a predetermined value, said low limit pressure signal comparator producing a second out of range signal on said output terminal of said low limit pressure signal comparator when pressure in said fluid conduit is lower than a predetermined value; and a determination circuit having a first input terminal in electrical communication with said output terminal of said high limit pressure signal comparator, a second input terminal in electrical communication with said output terminal of said low limit pressure signal comparator and an output terminal, said determination circuit producing a third out of range signal when either said high limit pressure output comparator produces a first out of range signal or said low limit pressure output comparator produces a second out of range signal, wherein said determination circuit is an OR gate having a first input terminal in electrical communication with said output terminal of said high limit pressure signal comparator, a second input terminal in electrical communication with said output terminal of said low limit pressure signal comparator, and an output terminal.

9. A sample probe obstruction detection device for detecting an obstruction in a sample probe of an automated fluid sample aspiration/dispensation device having said sample probe, a pump, and a fluid conduit connecting said sample probe and said pump, said sample obstruction detection device comprising:

a pressure sensor having a first output terminal, said pressure sensor positioned to measure pressure in said fluid conduit, said pressure sensor producing a signal representative of a pressure in said fluid conduit on said first output terminal;

an obstruction detection circuit providing a signal if said pressure sensor measures a pressure in said fluid conduit which is outside a predetermined pressure range at a predetermined amount of time following completion of one of an aspiration and a dispensation by said pump, said obstruction detection circuit comprising:

a high limit pressure signal comparator having a first input terminal in electrical communication with said first output terminal of said pressure sensor, a second input terminal in electrical communication with a first predetermined reference voltage, and an output terminal; and a low limit pressure signal comparator having an input terminal in electrical communication with said first output terminal of said pressure sensor, a second input terminal in electrical communication with a second predetermined reference voltage and an output terminal, said high limit pressure signal comparator producing a first out of range signal on said output terminal of said high limit pressure signal comparator when pressure in said fluid conduit is higher than a predetermined value, said low limit pressure signal comparator producing a second out of range signal on said output terminal of said low limit pressure signal comparator when pressure in said fluid conduit is lower than a predetermined value;

wherein said high limit pressure signal comparator and said low limit pressure signal comparators are tri-state devices and wherein said output terminal of said high limit pressure signal comparator is in electrical communication with said output terminal of said low limit pressure signal comparator.

10. A sample probe obstruction detection device for detecting an obstruction in a sample probe of an automated fluid sample aspiration/dispensation device having said sample probe, a pump, and a fluid conduit connecting said sample probe and said pump, said sample obstruction detection device comprising:

a pressure sensor having a first output terminal, said pressure sensor positioned to measure pressure in said fluid conduit, said pressure sensor producing a signal representative of a pressure in said fluid conduit on said first output terminal;

an obstruction detection circuit providing a signal if said pressure sensor measures a pressure in said fluid conduit which is outside a predetermined pressure range at a predetermined amount of time following completion of one of an aspiration and a dispensation by said pump, said obstruction detection circuit comprising:

a high limit pressure signal comparator having a first input terminal in electrical communication with said first output terminal of said pressure sensor, a second input terminal in electrical communication with a first predetermined reference voltage, and an output terminal; and a low limit pressure signal comparator having an input terminal in electrical communication with said first output terminal of said pressure sensor, a second input terminal in electrical communication with a second predetermined reference voltage and an output terminal, said high limit pressure signal comparator producing a first out of range signal on said output terminal of said high limit pressure signal comparator when pressure in said fluid conduit is higher than a predetermined value, said low limit pressure signal comparator producing a second out of range signal on said output terminal of said low limit pressure signal comparator when pressure in said fluid conduit is lower than a predetermined value;

an amplifier having a first input terminal in electrical communication with said first output terminal of said pressure sensor and an output terminal in electrical communication with said first input terminal of said high limit pressure comparator and in electrical communication with said first input terminal of said low limit pressure signal comparator; and an error amplifier having a first input terminal in electrical communication with said output terminal of said amplifier, a second input terminal in electrical communication with a third predetermined reference voltage, an output terminal; and a sample and hold circuit having an input terminal in electrical communication with said output terminal of said error amplifier, an output terminal in electrical communication with said first input terminal of said amplifier and a control terminal, said sample and hold circuit holding a signal value applied to said input terminal of said sample and hold circuit on said output terminal of said sample and hold circuit in response to a control signal applied to said control terminal of said sample and hold circuit.

11. The sample probe obstruction detection device of claim 10 wherein said first predetermined reference voltage, said second predetermined reference voltage and said third predetermined reference voltage is a voltage divider.

12. A sample probe obstruction detection device for detecting an obstruction in a sample probe of an automated fluid sample aspiration/dispensation device, said aspiration/dispensation device having, said sample probe, a pump and a fluid conduit connecting said sample probe and said pump, said sample obstruction detection device comprising:

a pressure sensor having a first output terminal and a second output terminal, said pressure sensor positioned in said fluid conduit, said pressure sensor producing a signal representative of a pressure in said fluid conduit on said first output terminal and said second output terminal;

a differential amplifier having first input terminal in electrical communication with said first output terminal of said pressure sensor, a second input terminal in electrical communication with said second output terminal of said pressure sensor and an output terminal;

a high limit pressure signal comparator having a first input terminal in electrical communication with said output terminal of said differential amplifier, a second input terminal in electrical communication with a first predetermined reference voltage, and an output terminal;

a low limit pressure signal comparator having an input terminal in electrical communication with said output terminal of said differential amplifier, a second input terminal in electrical communication with a second predetermined reference voltage and an output terminal;

an AND gate having a first input terminal in electrical communication with said output terminal of said high limit pressure signal comparator, a second input terminal in electrical communication with said output terminal of said low limit pressure signal comparator, and an output terminal;

an error amplifier having a first input terminal in electrical communication with said output terminal of said differential amplifier, a second input terminal in electrical communication with a third predetermined reference voltage; and a sample-and-hold circuit having an input terminal in electrical communication with said output terminal of said error amplifier, an output terminal in electrical communication with said first input terminal of said differential amplifier and a control terminal, said sample-and-hold circuit holding a signal value applied to said input terminal of said sample-and-hold circuit on said output terminal of said sample-and-hold circuit in response to a control signal applied to said control terminal of said sample-and-hold circuit, said high limit pressure signal comparator producing an out of range signal on said output terminal of said high limit pressure signal comparator when pressure in said fluid conduit is higher than a predetermined value, said low limit pressure signal comparator producing an out of range signal on said output terminal of said low limit pressure signal comparator when pressure in said fluid conduit is lower than a predetermined value, and said AND gate producing a first signal on said output terminal of said AND gate when at least one of said high limit pressure output comparator and said low limit pressure output comparator produces an out of range signal and producing a second signal on said output terminal of said output terminal of said AND gate when neither of said high limit pressure signal comparator and said low limit pressure signal comparator produces an out of range signal.

13. A method for determining whether a sample probe of an automated fluid sample aspiration/dispensation device is obstructed, said method comprising the steps of:

beginning one of a dispensation or an aspiration of a volume of fluid through said sample probe;

completing said one of a dispensation or an aspiration of said volume of fluid through said sample probe;

measuring a final pressure within said sample probe at a predetermined amount of time following said completion of said one of a dispensation or an aspiration; and signaling an error condition if said final pressure within said sample probe is outside upper and lower limits of a predetermined range.

14. A sample probe obstruction detection device for detecting an obstruction in a sample probe of an automated fluid sample aspiration/dispensation device having, said sample probe, a pump and a fluid conduit connecting said sample probe and said pump, said sample obstruction detection device comprising:

a pressure sensor having a first output terminal, said pressure sensor positioned to measure pressure in said fluid conduit, said pressure sensor producing a signal representative of a pressure in said fluid conduit on said first output terminal; and an obstruction detection circuit having a first input terminal in electrical communication with said first output terminal of said pressure sensor;

said obstruction detection circuit providing a first signal on an output terminal of said obstruction detection circuit if said pressure sensor measures a pressure in said fluid conduit which is outside upper and lower limits of a predetermined pressure range at a predetermined amount of time following completion of one of an aspiration and a dispensation by said pump.

\* \* \* \* \*